(12) United States Patent
Castro (10) Patent No.: US 6,267,763 B1
(45) Date of Patent: *Jul. 31, 2001

(54) METHOD AND APPARATUS FOR SPINAL IMPLANT INSERTION

(75) Inventor: Salvatore Castro, Seymour, CT (US)

(73) Assignee: Surgical Dynamics, Inc., Norwalk, CT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/282,863

(22) Filed: Mar. 31, 1999

(51) Int. Cl.$^7$ ................................................ A61B 17/56

(52) U.S. Cl. .................. 606/61; 606/90; 623/17

(58) Field of Search .................. 606/61, 80, 90; 623/17.11, 17.16

(56) References Cited

U.S. PATENT DOCUMENTS

| | | |
|---|---|---|
| D. 377,093 | 12/1996 | Michelson . |
| 3,486,505 | 12/1969 | Morrison . |
| 3,848,601 | 11/1974 | Ma et al. . |
| 3,867,932 * | 2/1975 | Huene ........................... 606/80 |
| 3,916,907 | 11/1975 | Peterson . |
| 4,059,115 | 11/1977 | Junashev et al. . |
| 4,328,593 | 5/1982 | Sutter et al. . |
| 4,501,269 | 2/1985 | Bagby . |
| 4,545,374 | 10/1985 | Jacobson . |
| 4,573,448 | 3/1986 | Kambin . |

(List continued on next page.)

FOREIGN PATENT DOCUMENTS

| | | |
|---|---|---|
| 43 28 690A1 | 3/1995 | (DE) . |
| 2706309 | 6/1993 | (FR) . |

OTHER PUBLICATIONS

"Unilateral Posterior Lumbar Interbody Fusion: Simplified Dowel Technique", Clinical Ortopedics and Related Research, Blume (1984) pp. 75–84.
Scientix Brochure, Cage CH, "Lumbar Spacing Cages".

(List continued on next page.)

Primary Examiner—Henry J. Recla
Assistant Examiner—Julian W. Woo (57) ABSTRACT

An apparatus for facilitating fusion of adjacent vertebrae, In one preferred embodiment, the apparatus for facilitating fusion of adjacent vertebrae includes a retractor and a retractor introducer. The retractor includes a retractor sleeve having proximal and distal ends and defines a longitudinal passageway for reception of surgical instrumentation. The retractor sleeve has first and second retractor arms extending distally therefrom in a general longitudinal direction. Each retractor arm has first and second opposed supporting surfaces for engaging respective adjacent opposed vertebrae. Each retractor arm defines a dimension between the first and second supporting surfaces sufficient to distract the opposed vertebrae upon insertion thereof. The retractor introducer is positionable within the longitudinal passageway of the retractor sleeve. The retractor introducer includes an elongated member defining proximal and distal ends and having a distal introducer head. The introducer head has a retractor arm insert. The retractor arm insert preferably defines a cross-sectional dimension to substantially occupy the inner area defined by the retractor arms of the retractor and possesses sufficient rigidity to advance within the tissue portions thereby facilitating placement of the first and second retractor arms of the retractor between the vertebral portions in distracting engagement therewith. The introducer head of the retractor introducer may also define a proximal portion which has a cross-sectional dimension generally corresponding to the internal dimension of the retractor sleeve to thereby substantially minimize entry of tissue within the retractor sleeve during placement between the opposed vertebrae. Preferably, the cross-sectional dimension of the proximal portion of the introducer head is slightly less than the internal dimension of the retractor sleeve.

17 Claims, 11 Drawing Sheets

U.S. PATENT DOCUMENTS

| | | |
|---|---|---|
| 4,677,972 | 7/1987 | Tornier . |
| 4,743,256 | 5/1988 | Brantigan . |
| 4,834,757 | 5/1989 | Brantigan . |
| 4,877,020 | 10/1989 | Vich . |
| 4,878,915 | 11/1989 | Brantigan . |
| 4,936,851 | 6/1990 | Fox et al. . |
| 4,961,740 | 10/1990 | Ray et al. . |
| 4,978,350 | 12/1990 | Wagenkencht . |
| 5,015,247 | 5/1991 | Michelson . |
| 5,015,255 | 5/1991 | Kuslich . |
| 5,026,373 | 6/1991 | Ray et al. . |
| 5,055,104 | 10/1991 | Ray . |
| 5,062,845 | 11/1991 | Kuslich et al. . |
| 5,195,541 | 3/1993 | Obenchain . |
| 5,263,953 | 11/1993 | Bagby . |
| 5,313,962 | 5/1994 | Obenchain . |
| 5,352,231 | 10/1994 | Brumfield et al. . |
| 5,354,302 | 10/1994 | Ko . |
| 5,357,983 | 10/1994 | Mathews . |
| 5,358,511 | 10/1994 | Gatturna et al. . |
| 5,395,317 | 3/1995 | Kambin . |
| 5,423,825 | 6/1995 | Levine . |
| 5,431,658 | 7/1995 | Moskovich . |
| 5,439,464 | 8/1995 | Shapiro . |
| 5,454,811 | 10/1995 | Huebner . |
| 5,470,334 | 11/1995 | Ross et al. . |
| 5,480,403 | 1/1996 | Lee et al. . |
| 5,484,437 | 1/1996 | Michelson . |
| 5,489,307 | 2/1996 | Kuslich et al. . |
| 5,505,732 * | 4/1996 | Michelson ............................... 606/61 |
| 5,554,191 | 9/1996 | Lahille et al. . |
| 5,562,736 | 10/1996 | Ray et al. . |
| 5,571,109 | 11/1996 | Bertagnoli . |
| 5,571,189 | 11/1996 | Kuslich . |
| 5,591,207 | 1/1997 | Coleman . |
| 5,609,636 | 3/1997 | Kohrs et al. . |
| 5,722,977 * | 3/1998 | Wilhelmy ............................... 606/61 |
| 5,772,661 | 6/1998 | Michelson . |
| 5,782,919 | 7/1998 | Zdeblick et al. . |
| 5,797,909 | 8/1998 | Michelson . |
| 5,885,299 | 3/1999 | Winslow et al. . |
| 5,928,242 | 7/1999 | Kuslich et al. . |

OTHER PUBLICATIONS

Surgical Dynamics Brochure, Ray Ti for Interbody Fusion, Investigational Device, (1994).

"Laparoscopic Bone Dowel Sugical Technique", Sofamor Danek.

"BAK Biomcheanical Rationale", Spinetech, Inc.

"BAK Cervical Interbody Fusion System", Spinetech, Inc.

Stryker Implants Brochure, Ogival Interbody Cage, Surgical Technique.

* cited by examiner

METHOD AND APPARATUS FOR SPINAL IMPLANT INSERTION

BACKGROUND

1. Technical Field

The present disclosure generally relates to a method and associated instrumentation for implant insertion and, in particular, to a method and instrumentation for insertion of a spinal implant to facilitate fusion of adjacent vertebral bodies.

2. Background of the Related Art

A large number of orthopedic procedures involve the insertion of either natural or prosthetic implants into bone or associated tissues. These procedures include, for example, ligament repair, joint repair or replacement, non-union fractures, facial reconstruction, spinal stabilization and spinal fusion. In a typical procedure, an insert, dowel or screw is inserted into a prepared bore formed in the bone or tissues to facilitate repair and healing. See, for example, U.S. Pat. Nos.: U.S. Pat. No. 5,470,334 to Ross et al.; U.S. Pat. No. 5,454,811 to Huebner; U.S. Pat. No. 5,480,403 to Lee et al.; U.S. Pat. No. 5,358,511 to Gatturna et al.; and U.S. Pat. No. 4,877,020 to Vich.

Some implants are particularly configured with cavities and bores to facilitate bony ingrowth and enhance anchoring of the implant at the insertion site. See, for example, U.S. Pat. No. 4,328,593 to Sutter et al.; U.S. Pat. No. 4,936,851 to Fox et al.; and U.S. Pat. No. 4,878,915 to Brantigan. Other specialized implants include fusion cages having internal cavities to receive bone growth stimulation materials such as bone chips and fragments. See, for example, U.S. Pat. Nos.: U.S. Pat. No. 4,501,269 to Bagby; U.S. Pat. No. 4,961,740 to Ray et al.; U.S. Pat. No. 5,015,247 to Michelson; and U.S. Pat. No. 5,489,307 to Kuslich et al. These types of implants are particularly well suited for intervertebral spinal fusion procedures necessitated by injury, disease or some degenerative disorder of the spinal disc. Subsequently, there may be progressive degeneration leading to mechanical instability between adjacent vertebrae necessitating direct fusion of the vertebrae while maintaining a pre-defined intervertebral space. This fusion may be accomplished by the insertion of one or more of the specialized implants as discussed above and also discussed in commonly assigned U.S. Pat. No. 5,026,373, the contents of which are incorporated herein by reference.

Both anterior (transabdominal) and posterior surgical approaches are used for interbody fusions of the lumbar spine. Fusions in the cervical area of the spine are primarily performed using posterior and approaches as well. Typically, an implant such as a plug, dowel, prosthesis or cage is inserted into a preformed cavity inside the interbody, interdiscal space. Since it is desirable in these procedures to promote a "bone to bone" bridge, connective tissue and at least a portion of the distal tissue is removed. Preferably, relatively deep cuts are made in the adjacent bones in order to penetrate into the softer, more vascularized cancellous region to facilitate bone growth across the implant.

One of the more critical tasks performed in the insertion of a surgical fusion implant, particularly, in intervertebral spinal fusion, is the formation of the implant receiving cavity or bore within the adjacent vertebrae. More particularly, the drilled bore must be equally centered within the intervertebral space and preferably parallel to the vertebral end plates to ensure removal of equal portions of bone from the adjacent vertebrae throughout the length of the cut and subsequent appropriate seating of the implant relative to the vertebral bodies.

Surgical instruments for facilitating spinal fusion implant insertion are known. For example, U.S. Pat. No. 5,484,437 to Michelson discloses a method and apparatus incorporating an outer and an inner sleeve arrangement. The outer sleeve has teeth at one end which are driven directly into the posterior surface of the adjacent vertebrae. The inner sleeve is positioned within the outer sleeve and serves to guide instruments such as a drill used to form the implant receiving bore. U.S. Pat. No. 5,487,307 to Kuslich et al.; U.S. Pat. No. 5,015,247 to Michelson; and U.S. Pat. No. 4,878,915 to Brantigan disclose similar arrangements. Other arrangements include the use of guide rods which are placed in pilot holes formed in the vertebral bodies. The guide rods guide a bore forming hollow drill into the intervertebral space.

Although current instrumentation and methods associated therewith for enhancing the placement of spinal fusion implants have been generally effective for their intended purposes, there exists certain limitations with the design of this instrumentation which detract from their usefulness. For example, the arrangement disclosed in the Michelson '437 patent and similar arrangements do not provide for automatic alignment of the outer sleeve to ensure that the bore formed by a drill introduced into the outer sleeve is in optimal alignment for a tapping procedure (if required) and reception of the spinal implant. Rather, such orientation is dependent directly upon the skill of the surgeon. Moreover, the outer sleeve, which is mounted only at its extreme distal end to the posterior surface of the adjacent vertebrae, is subject to disorientation or dislodgment during insertion and/or removal of the drill and/or tapping instrument. Similarly, the use of guide rods increases the number of steps required to implant the fusion cage and is also subject to possible misalignment.

Commonly assigned U.S. patent application Ser. No. 08/889,661, filed Jul. 8, 1997, which claims priority to Ser. No. 08/615,379, filed Mar. 14, 1996, the contents of which are incorporated herein by reference, discloses a unique method and instrumentation for effecting fusion of adjacent vertebral bodies. The method and instrumentation incorporates a retractor, commercially known as the USSC Tang Retractor, which performs several functions upon its placement between adjacent bodies. Specifically, the USSC Tang Retractor is advantageously configured to: 1) distract the adjacent vertebrae a desired predetermined special distance to facilitate the insertion and application of an implant therethrough; 2) provide a cannula for reception of other instrumentation needed to perform the procedure; and 3) ensure accurate alignment of the instruments and accurate insertion of the implant.

SUMMARY

Accordingly, the present disclosure is directed to further improvements in connection with the USSC Tang Retractor and its application in spinal fusion. In one preferred embodiment, the apparatus for facilitating fusion of adjacent vertebrae includes a retractor and a retractor introducer. The retractor includes a retractor sleeve having proximal and distal ends and defines a longitudinal passageway for reception of surgical instrumentation. The retractor sleeve has first and second retractor arms extending distally therefrom in a general longitudinal direction. Each retractor arm has first and second opposed supporting surfaces for engaging respective adjacent opposed vertebrae. Each retractor arm defines a dimension between the first and second supporting surfaces sufficient to distract the opposed vertebrae upon insertion thereof. The retractor introducer is positionable within the longitudinal passageway of the retractor sleeve.

The retractor introducer includes an elongated member defining proximal and distal ends and having a distal introducer head. The introducer head has a retractor arm insert. The retractor arm insert preferably defines a cross-sectional dimension to substantially occupy the inner area defined by the retractor arms of the retractor and possesses sufficient rigidity to advance within the tissue portions thereby facilitating placement of the first and second retractor arms of the retractor between the vertebral portions in distracting engagement therewith. The introducer head of the retractor introducer may also define a proximal portion which has a cross-sectional dimension generally corresponding to the internal dimension of the retractor sleeve to thereby substantially minimize entry of tissue within the retractor sleeve during placement between the opposed vertebrae. Preferably, the cross-sectional dimension of the proximal portion of the introducer head is slightly less than the internal dimension of the retractor sleeve.

The retractor introducer may include engaging structure to cooperate with corresponding engaging structure of the retractor sleeve to rotatably fix the retractor introducer and retractor sleeve. The engaging structure of the retractor introducer includes at least one pin which is receivable within a corresponding groove of the retractor sleeve. The retractor introducer may include a first flange intermediate the proximal and distal end portions of the elongated member. The first flange is in contacting engagement with the proximal end of the retractor sleeve wherein the retractor introducer and retractor sleeve move concurrently during placement within the opposed vertebrae. The retractor introducer may include a second flange adjacent the proximal end of the elongated member and dimensioned to receive impact of a hammer.

The retractor sleeve may include at least one longitudinal opening in communication within the longitudinal passageway to receive surgical instrumentation. The retractor sleeve includes at least one longitudinal planar surface portion to minimize a cross-sectional dimension of the retractor sleeve to facilitate placement in the restricted intervertebral space area. Preferably, the retractor sleeve includes diametrically opposed longitudinal planar surface portions.

A method for performing a surgical procedure is also disclosed. The method includes the steps of providing a surgical retractor including a sleeve member defining a longitudinal axis, the sleeve member including proximal and distal end portions and defining an axial opening therethrough to receive instrumentation, the distal end portion configured for insertion at least partially into an intervertebral space between adjacent opposed vertebrae and having two spaced apart retractor arms, each retractor arm including first and second supporting surfaces laterally displaced with respect to each other and to the longitudinal axis;

positioning a retractor introducer within the axial opening of the retractor, the retractor introducer including an elongated member having a distal introducer head, the distal introducer head having a retractor arm insert arranged to be disposed between the retractor arms of the retractor sleeve in the mounted condition of the retractor introducer and having sufficient rigidity to facilitate advancement within tissue;

impacting the proximal end of the retractor introducer to drive the retractor arm insert of the retractor introducer and the retractor arms of the retractor within the intervertebral space whereby the first supporting surface of each retractor arm engages one vertebrae and the second supporting surface of each retractor arm engages the other vertebrae such that the adjacent opposed vertebrae are laterally displaced whereby the retractor arm insert facilitates entry of the retractor arms into the intervertebral space;

removing the retractor introducer; and performing the surgical spinal procedure.

BRIEF DESCRIPTION OF THE DRAWINGS

Preferred embodiments of the disclosure are described hereinbelow with reference to the drawings wherein.

DETAILED DESCRIPTION OF THE PREFERRED EMBODIMENT(S)

The preferred embodiments of the method and instrumentation disclosed herein are discussed in terms of orthopedic spinal fusion procedures and instrumentation. It is also envisioned, however, that the disclosure is applicable to a wide variety of procedures including, but not limited to ligament repair, joint repair or replacement, non-union fractures, facial reconstruction and spinal stabilization. In addition, it is believed that the present method and instrumentation finds application in both open and minimally invasive procedures including endoscopic and arthroscopic procedures wherein access to the surgical site is achieved through a cannula or small incision.

The following discussion will include a description of each instrument utilized in performing a spinal fusion method followed by a description of the preferred method for spinal fusion utilizing the instrumentation in accordance with the present disclosure.

In the discussion which follows, the term "proximal", as is traditional, will refer to the portion of the structure which is closest to the operator, while the term "distal" will refer to the portion which is furthest from the operator.

Figure 1:
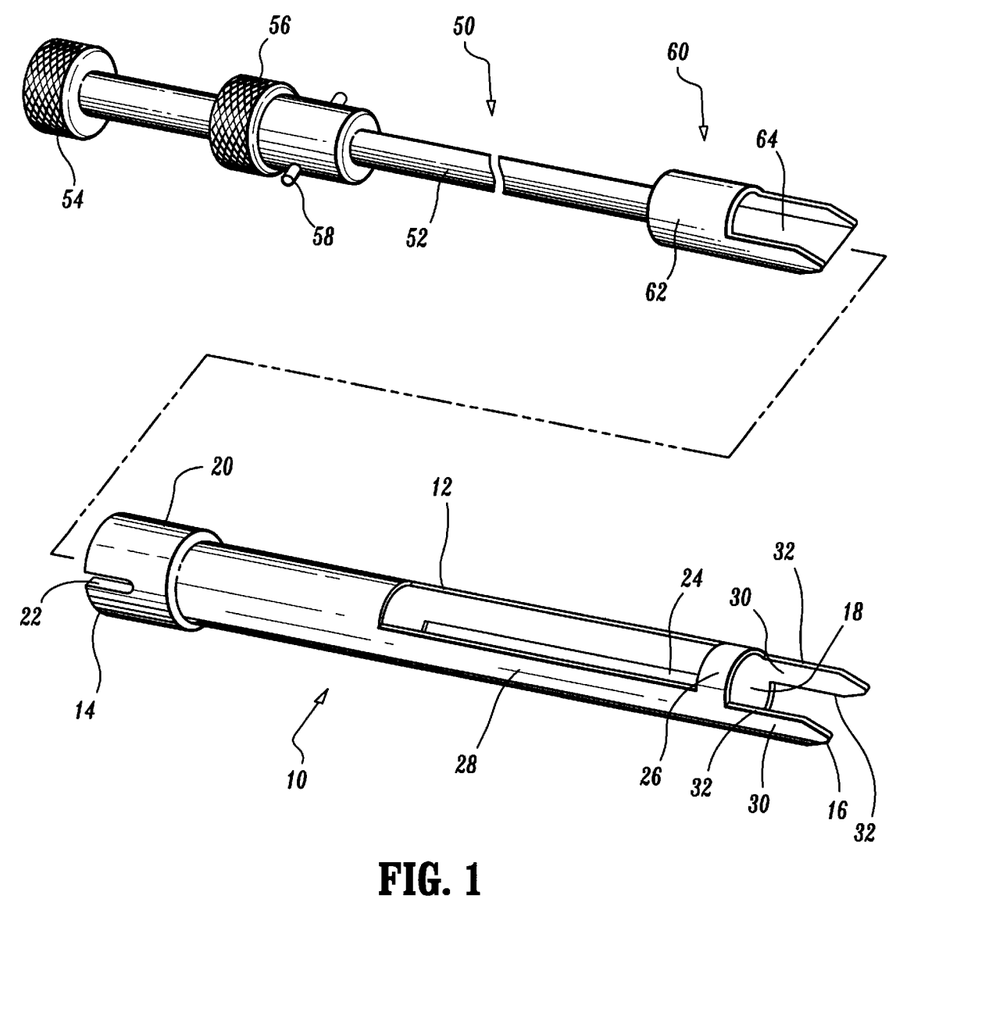
FIG. 1 illustrates a surgical retractor and retractor introducer constructed in accordance with the principles of the present disclosure and utilized in distracting adjacent bony structures particularly adjacent vertebrae.

Referring now to the drawings in which like reference numerals identify similar or identical elements throughout the several views, FIG. 1 illustrates in perspective view a preferred embodiment of the surgical retractor and retractor introducer of the present disclosure. Retractor 10 and retractor introducer 50 are particularly contemplated for distracting adjacent bony structures, e.g., adjacent vertebral bodies, to facilitate the insertion and application of a spinal implant. However, it is envisioned that the instrumentation may also be utilized to distract other structures as well including joints, ligaments, etc . . . . Other applications for the instrumentation are also contemplated.

Figure 2:
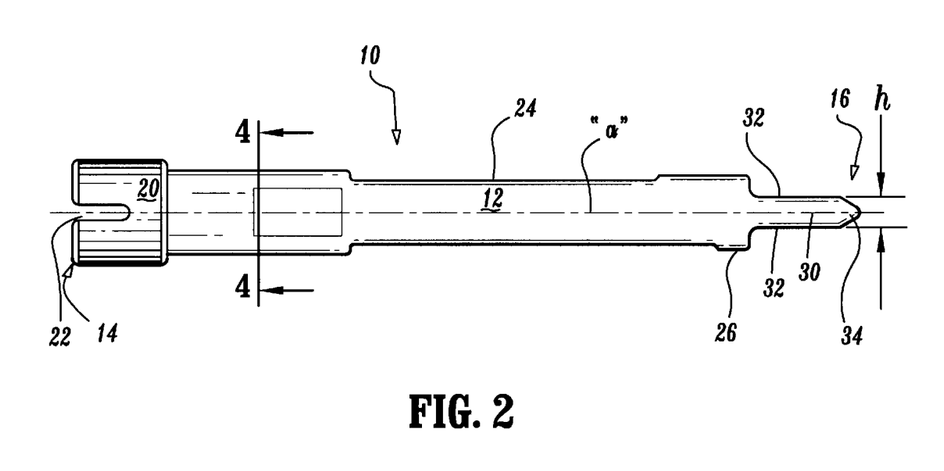
FIG. 2 is a side plan view of the retractor of FIG. 1.
Figure 3:
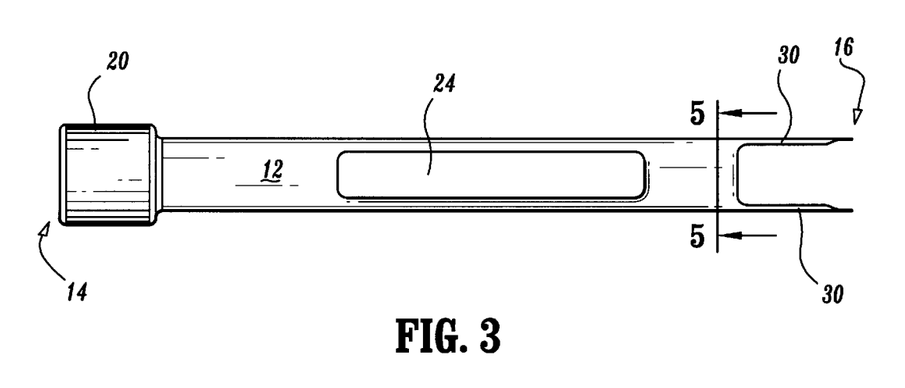
FIG. 3 is a top plan view of the retractor.

Referring now to FIGS. 1–2, retractor 10 will be discussed. Retractor 10 is similar in configuration to the retractor sleeve disclosed in commonly assigned U.S. patent application Ser. No. 08/615,379, filed Mar. 14, 1996, the contents of which have been already incorporated herein by reference. Retractor 10 may be a variety of sizes including 12 mm, 14 mm, 16 mm and 18 mm in diameter. The retractor size utilized will generally correspond to the size of the fusion implant to be positioned within the intervertebral space of adjacent vertebrae. Retractor 10 may be formed of any suitable rigid material including stainless steel, titanium, aluminum or a suitable polymeric material and formed by injection molded techniques.

With reference now to FIGS. 1–5, retractor 10 includes retractor sleeve 12 defining proximal and distal ends 14, 16 and having a longitudinal bore 18 extending completely through its length. Retractor sleeve 12 includes collar 20 adjacent its proximal end 14. Collar 20 has a pair of longitudinal recesses 22 formed in its outer wall surface. Retractor sleeve 12 further includes first and second longitudinally extending openings 24 in its outer wall and extending in communication with longitudinal bore 18. Openings 24 are diametrically arranged with relation to each other and terminate at their distal ends in circumferential collar 26. Each opening 24 extends radially for about between 15%–40% the circumference or perimeter of sleeve 12 and longitudinally for about 40%–60% the length of sleeve 12. Openings 24 are contemplated to permit the introduction of surgical instrumentation required to carry out the fusion procedure.

Figure 4:
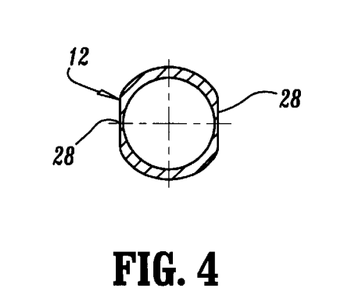
FIG. 4 is a cross-sectional view of the retractor taken along the lines 4—4 of FIG.2.
Figure 5:
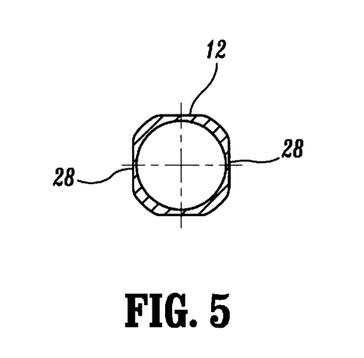
FIG. 5 is a cross-sectional view of the retractor taken along the lines 5—5 of FIG.3.

With reference to the cross-sectional views of FIGS. 4–5, the outer wall of retractor sleeve 12 defines opposed planar surfaces 28. Planar surfaces 28 reduce the overall cross-section of retractor sleeve 12 thereby facilitating positioning of retractor sleeve 12 in the restricted vertebral locale. Planar surfaces 28 also permit two retractor sleeves 12 to be placed in side-by-side relation if desired to effectuate simultaneous placement of a pair of implants.

Retractor sleeve 12 further includes first and second diametrically opposed retractor arms 30. Retractor arms 30 extend in a general longitudinal direction and are spaced from each other. Each retractor arm 30 has first and second supporting surfaces 32 in general parallel relation to each other and preferably to the longitudinal axis "a" of sleeve 12. The height "h" of each arm 30 (i.e., the distance between supporting surfaces 32) corresponds to the height of the space between adjacent bony structures to be distracted. For example, in spinal fusion application, the height "h" of each arm 30 ranges from about 0.28 to about 0.35 inches. Each arm 30 further includes tapered end portions 34 defining a generally V-shaped configuration. End portions 34 facilitate insertion of retractor arms 30 within the surgical site, e.g., within the intervertebral space.

Figure 6:
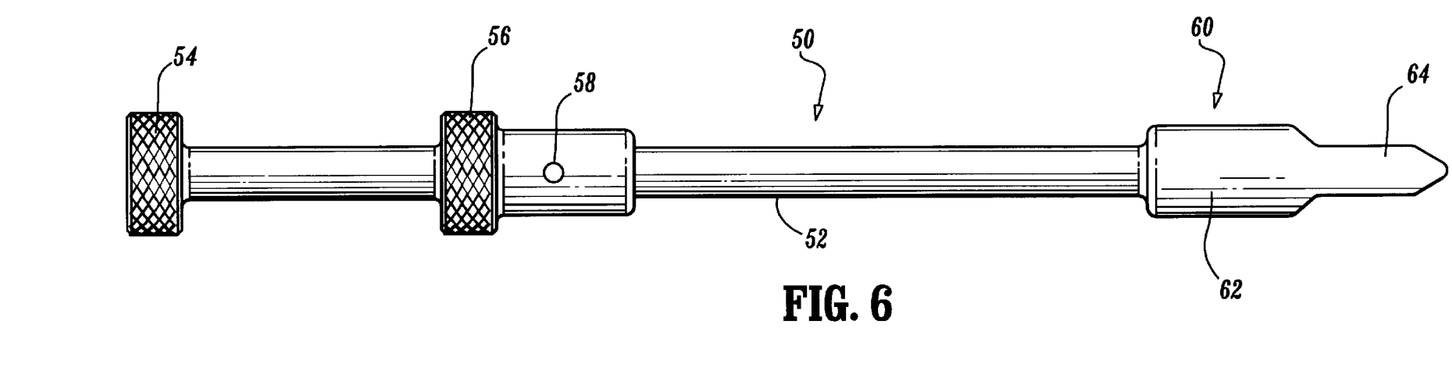
FIG. 6 is a side plan view of the retractor introducer.
Figure 7:
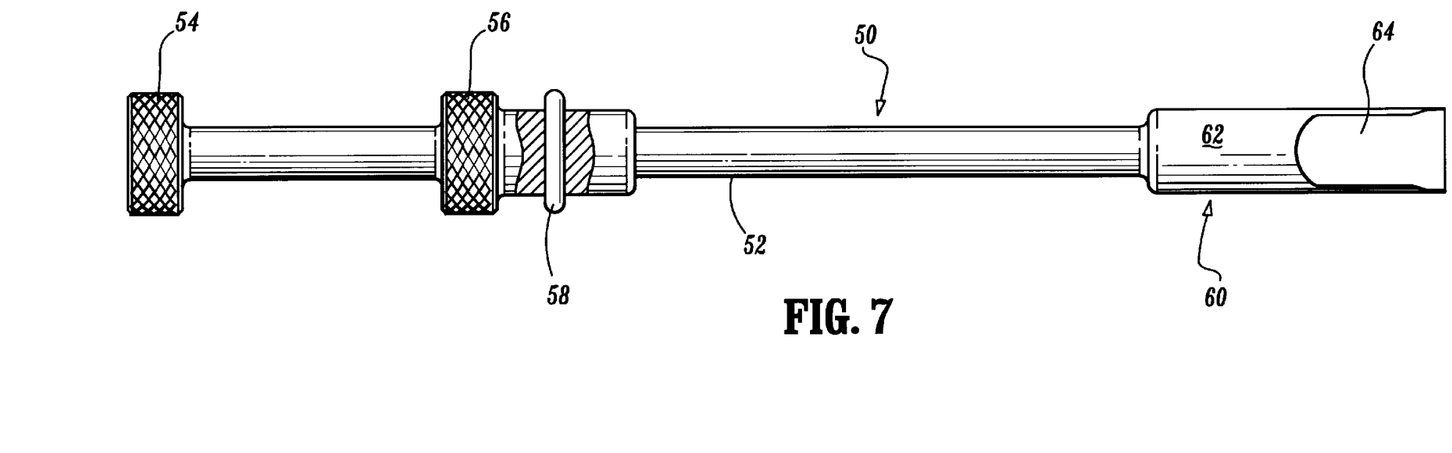
FIG. 7 is a top plan view of the retractor introducer.

With reference now to FIGS. 6–7, in conjunction with FIG. 1, retractor introducer 50 will be discussed in detail. Retractor introducer 50 facilitates entry of retractor 10 within the intervertebral space. Retractor introducer 50 includes elongate member 52 having first and second proximally positioned spaced flanges 54, 56 and a transverse mounting pin 58 adjacent the flange 56. Flanges 54, 56 may have a knurled outer surface to facilitate gripping engagement therewith. Retractor introducer 50 further includes an introducer head 60 at the distal end portion of the elongate member 52. Introducer head 60 includes proximal cylindrical portion 62 and a distal arm insert 64. Proximal cylindrical portion 62 defines a generally circular cross-section having a dimension slightly less than the internal diameter of retractor sleeve 12. Thus, in the assembled condition of retractor introducer 50 within retractor 12, proximal cylindrical portion 62 substantially occupies the internal area of retractor sleeve 12. This arrangement substantially minimizes entry of tissue within retractor sleeve 12 as will be discussed. Arm insert 64 of introducer head 60 is a solid structure configured to generally correspond to, and occupy, the inner boundary defined by retractor arms 30 of retractor 10. Arm insert 64 is substantially rigid and functions to increase the effective rigidity of retractor arms 30 thereby facilitating entry into the adjacent bone structures.

In the assembled condition of retractor introducer 50 within retractor 10, retractor introducer 50 is inserted within retractor 10 and positioned such that flange 56 of retractor introducer 50 abuts the proximal end face of retractor 10 with transverse mounting pin 58 received within the longitudinal recesses 22 of the retractor 10 and distal arm insert 64 disposed within the inner boundary defined by retractor arms 28. Proximal flange 54 receives the impact of a mallet used to position the elongated retractor arms 28 of retractor 10 within the intervertebral space.

Figure 14:
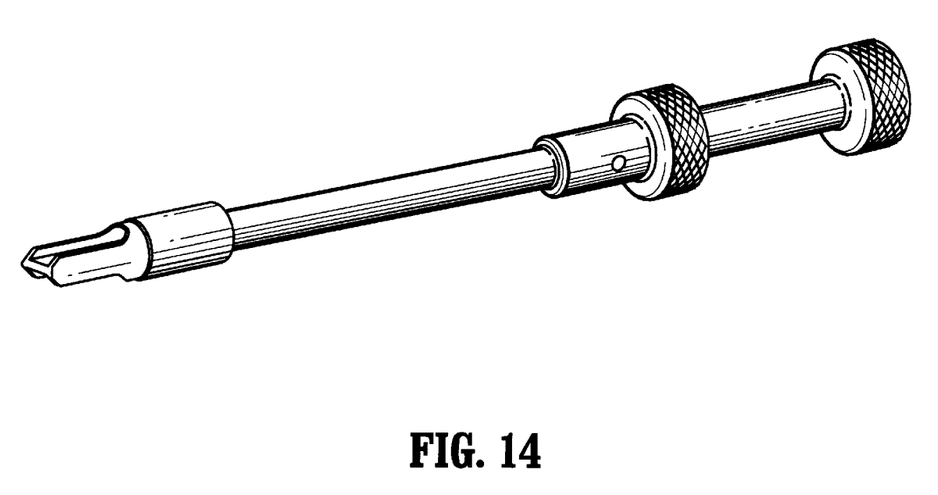
FIG. 14 is a perspective view of an alternate embodiment of the retractor introducer of the present disclosure.
Figure 15:
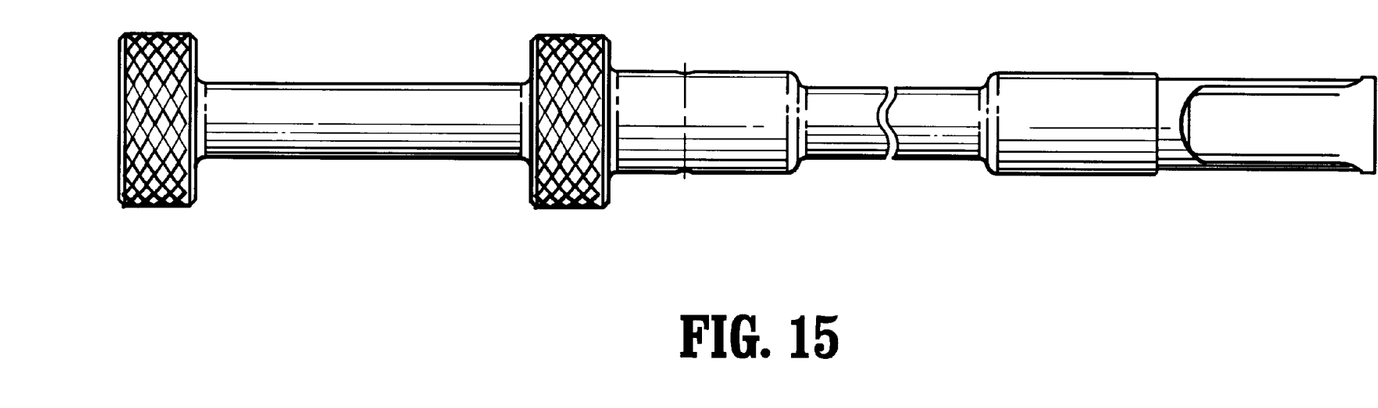
FIG. 15 is a top plan view of the retractor introducer of FIG. 14.
Figure 16:
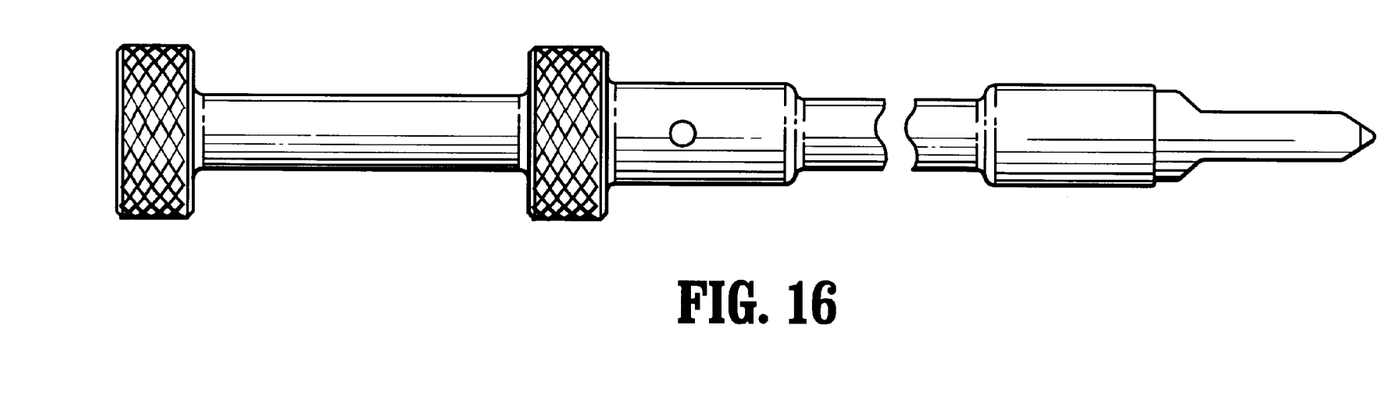
FIG. 16 is a side view of the retractor introducer of FIG. 14.

FIGS. 14–16 illustrate an alternate preferred embodiment of the tang introducer, designated generally by reference numeral 10'. Tang introducer 10' is identical to tang introducer 50' of FIG. 1 except for 1) the provision of feet or spacers 53a, and 53b and 2) the reduced height h of arm insert 64'. Feet 53a, 53b at the distal tip provide sufficient support for the retractor arms 30, but create a gap between the remaining portions of retractor introducer 50' and the retractor arms 30. This facilitates removal of the retractor introducer 50' after placement of the retractor 10.

Height h of arm insert 64' is slightly less than the height of the retractor arms 30. This avoids contact of the arm insert 64' with the end plates, thereby reducing damage in the area where end plate preparation will occur.

Retractor introducer 50 may be formed of any suitable rigid material including stainless steel, titanium, aluminum or a suitable polymeric material and formed by injection molded techniques.

Figure 8:
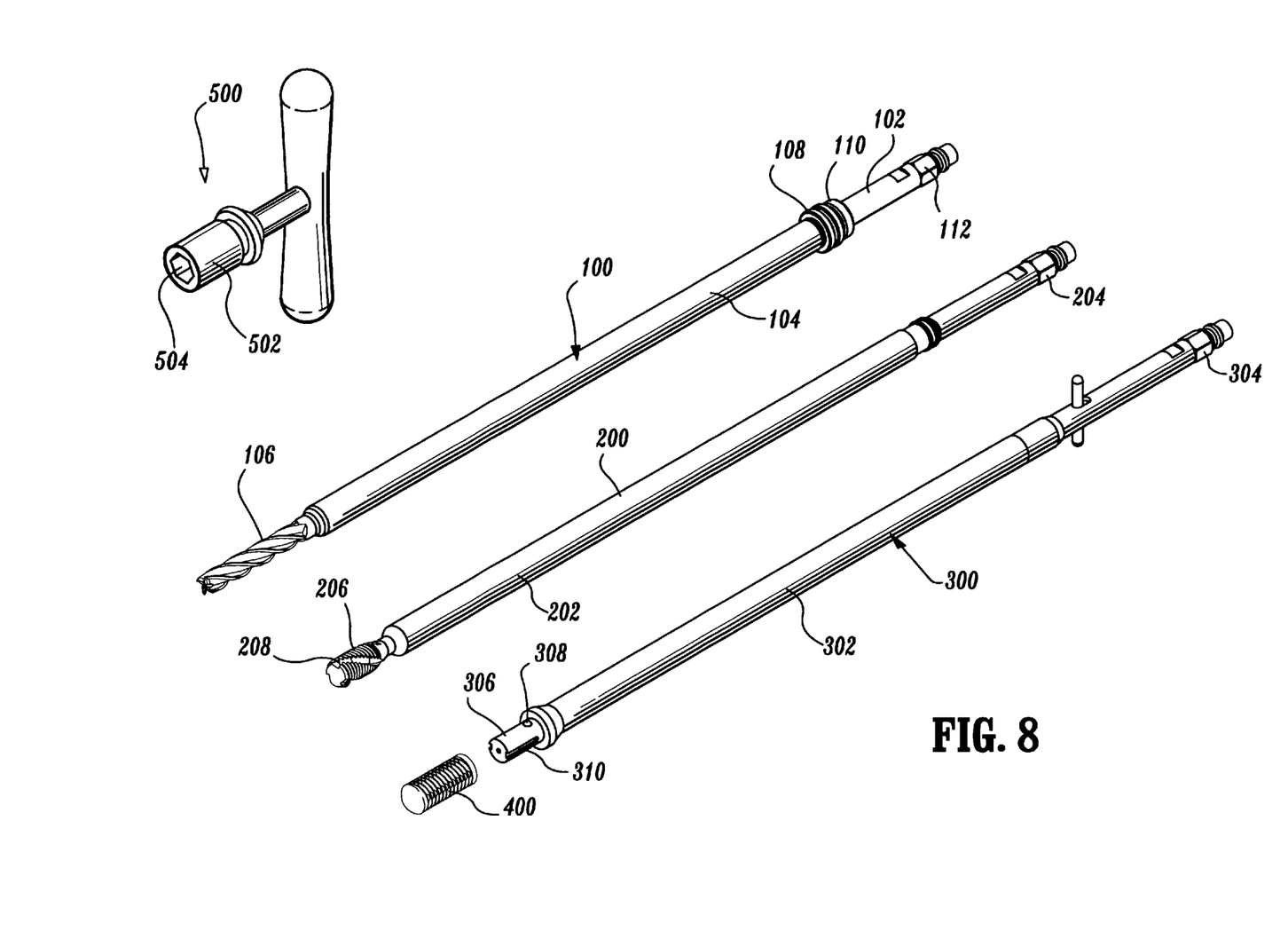
FIG. 8 is a perspective view of a surgical instrumentation for performing a spinal fusion procedure illustrating, from bottom to top, a spinal implant, an implant insertion apparatus, a surgical tap instrument, a drill instrument and a T-shaped handle.

Referring now to FIG. 8, the various instruments utilized in performing a spinal fusion procedure with the retractor 10 of the present disclosure are illustrated. These instruments include surgical drill 100, tap instrument 200, implant insertion instrument 300, fusion implant 400 and T-shaped handle 500 which is used to actuate each of the instruments.

Surgical drill 100 is disclosed in the previously incorporated '379 application. Drill 100 includes drill shaft 102, extension shaft 104 and drill bit 106 mounted at the distal end of the drill shaft 102. Extension shaft 104 has first and second collars 108, 110 which cooperate to control the depth of penetration of drill shaft 102 and drill bit 106 into the adjacent vertebrae. Drill shaft 102 includes a hexagonal-shaped head 112 at its proximal end to mount T-handle 500.

Tap instrument 200 is also disclosed in the '379 application. Tap instrument 200 is utilized for forming an internal thread within the drilled bore formed by the drill instrument 100. Tap instrument 200 includes elongated member 202 having hex head 204 at its proximal end to engage T-shaped handle 500. Tap instrument 200 further includes distal tapping threaded portion 206. Distal tapping portion 206 includes a plurality of conveyance channels (one is shown) 208 extending longitudinally through the cutting thread. Each conveyance channel 208 has a directional component parallel to the longitudinal axis and a directional component transverse to the longitudinal axis. Each conveyance channel 208 encompasses approximately an arc of about ⅓ the outer circumference of the tapping portion 206. Conveyance channels 208 are each dimensioned to receive bone material deburred by the cutting edges during the tapping procedure and to continually transmit the bone material proximally through the channel to avoid undesired material build up at the tapping site. In this manner, tap instrument 200 may be used to completely tap the internal thread within the bore without interruption of the tapping procedure.

Implant insertion instrument 300 is configured for mounting and inserting fusion implant 400 within the intervertebral space. Insertion instrument 300 includes elongated shaft 302 having hex-head mounting section 304 at its proximal end and cylindrical collar 306 at its distal end. Cylindrical collar 306 is dimensioned to be received within the cavity of fusion implant 400. A spring ball detent mechanism 308 is disposed within cylindrical collar 306 to releasably engage implant 400. Detent mechanism 308 is preferably spring-biased outwardly to engage corresponding structure defined within fusion implant 400 such as a recess or aperture formed in an interior wall thereof. Any type of detent mechanism 308 suitable for this intended purpose may be utilized. Collar 306 may further include a pair of longitudinal grooves 310 which engage corresponding structure of implant 400 (e.g., inner longitudinal rails) to rotatably fix the implant on the collar, i.e., to prevent rotational movement of the implant 400 on the collar. Other insertion instruments and arrangements are also envisioned.

Implant 400 is uniquely designed for use in spinal fusion procedures. This implant 400 is generally disclosed in U.S. Pat. No. 5,026,373 to Ray, the contents of which have been previously incorporated herein by reference, and is commonly referred to as a "fusion cage". Implant or fusion cage 400 includes a cylindrical cage body 402 having an internal cavity or hole for accommodating bone-growth inducing substances. One end of cage body 402 is closed and defines a rounded or bull-nosed configuration to facilitate insertion of the fusion cage relative to one or more bony structures. The other end defines an opening which communicates with the internal cavity. The outer surface of the cage body 402 includes a single continuous thread (preferably V-shaped) having a plurality of raised turns with valleys defined between adjacent turns. A plurality of perforations are disposed within the threads and extend through the outer surface of the cage body 402 to provide direct communication between the outer surface and internal cavity. The perforations permit immediate contact between the bone growth inducing substances within the inner cavity and the bone structure when the cage body 402 is mated to the bone structure, e.g., adjacent vertebrae. An end cap (not shown) may be mountable to the open end of cage body 402 to enclose the bone-growth inducing substances within the interior cavity.

T-shaped handle 500 includes mounting portion 502 defining hexagonal-shaped recess 504 which receives the corresponding structure of drill instrument 100, tap instrument 200 and implant insertion instrument 300.

Operation of the Instrumentation

The use of the instrumentation in conjunction with the insertion of a pair of fusion implants 400 into an intervertebral space defined between adjacent vertebrae will be described. The subsequent description will be particularly focused on an anterior procedure for spinal surgery although a posterior approach is envisioned as well.

Figure 9:
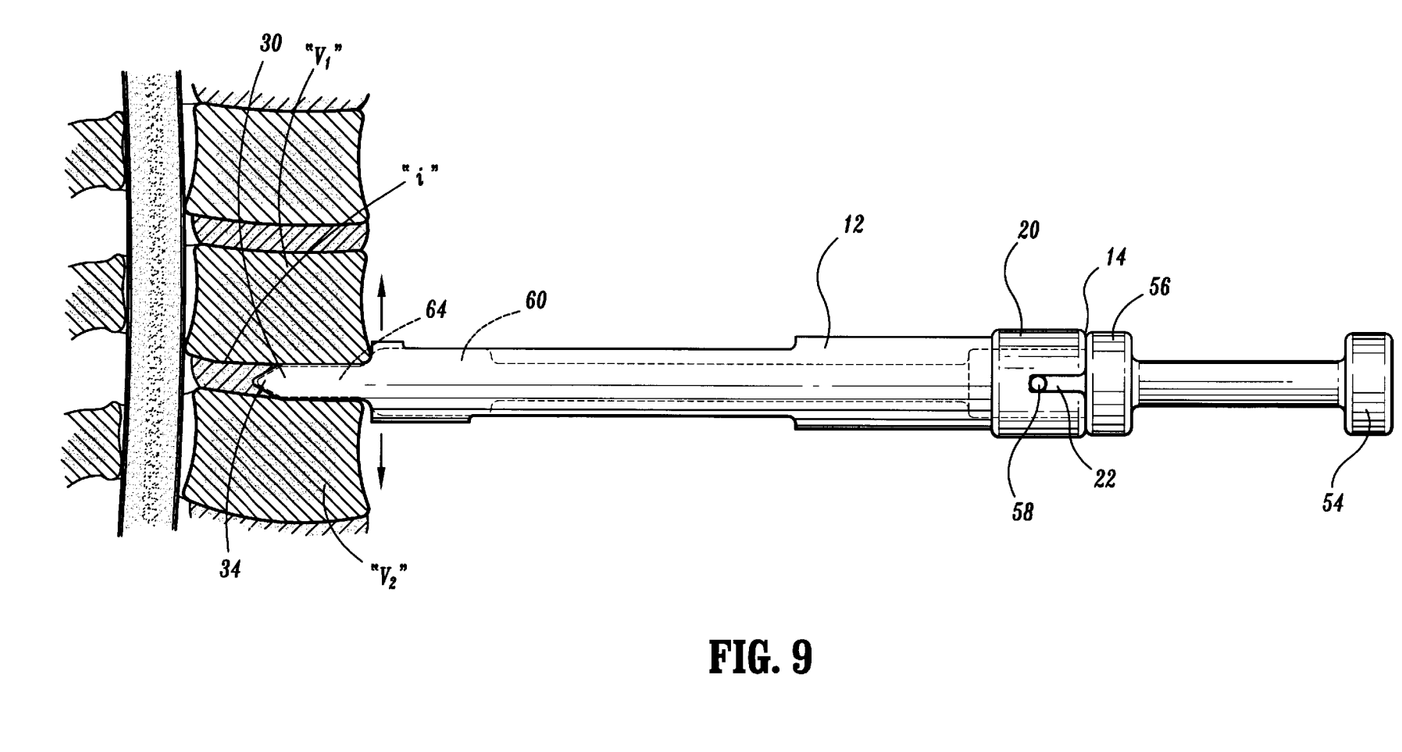
FIG. 9 is a side view illustrating insertion of the retractor and retractor introducer of FIG. 1 within an intervertebral space defined between adjacent vertebrae.

With reference to FIG. 9, which depicts a portion of the vertebral column, a targeted intervertebral space "i" defined between adjacent vertebrae "$V_1$, $V_2$" is accessed utilizing appropriate retractors, e.g., laminal retractors, dural extractors. As depicted in FIG. 9, retractor introducer 50 (shown in phantom) is positioned within retractor 10 and advanced within the retractor 10 such that flange 56 abuts the proximal end 14 of retractor sleeve 12 with transverse mounting pin 58 received within longitudinal recesses 22 of collar 20. (Retractor introducer 50' can be used in an identical manner) Thereafter, flange 54 is impacted with a mallet to drive retractor introducer 50 and retractor 10 distally toward the intervertebral space "i" with distal arm insert 64 of introducer head 60 and retractor arms 28 of retractor entering the space "i". Tapered end portions 20 of retractor arms 18 facilitate advancement within the intervertebral space "i". Arm insert 64 provides sufficient rigidity to support retractor arms 30 and facilitate entry of the retractor arms 30 between the adjacent vertebrae. As discussed above, proximal cylindrical portion 60 substantially minimizes entry of fluids and tissue within retractor sleeve 12.

Retractor arms 30 are advanced into the intervertebral space "i" whereby first and second supporting surfaces 32 respectively engage the opposed vertebral bodies "$V_1$, $V_2$". Retractor arms 30 are preferably dimensioned to slightly distract the adjacent vertebrae "$V_1$, $V_2$". However, it is envisioned that retractor arms 30 may be configured to cause no distracting movement of the vertebrae "$V_1$, $V_2$". Once inserted, retractor arms 30 effectively stabilize the adjacent vertebrae "$V_1$, $V_2$" across the span of the intervertebral space "i". Retractor introducer 50 is thereafter removed.

Figure 10:
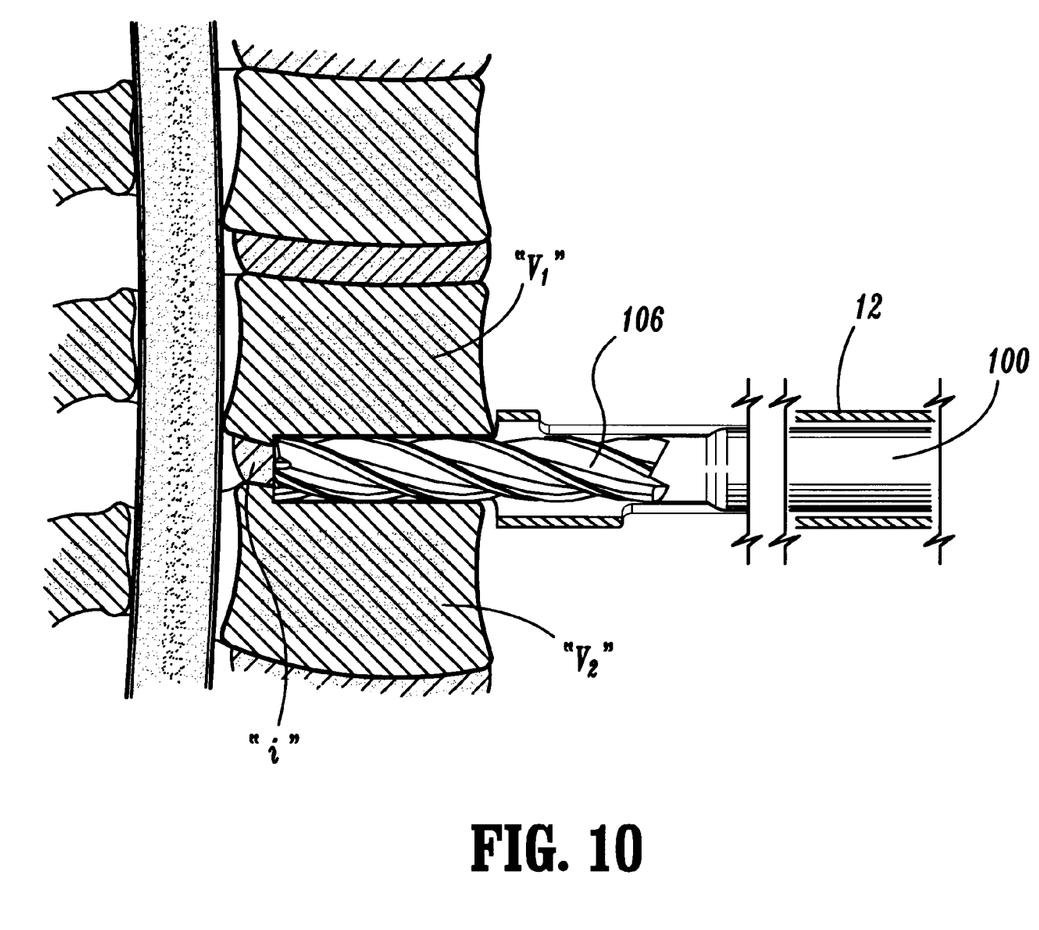
FIG. 10 is a side cross-sectional illustrating insertion of the drill instrument through the retractor to drill a bore adjacent a first lateral side of the adjacent vertebrae.

Referring now to FIG. 10, with retractor arms 30 of retractor sleeve 12 in its appropriate position within the intervertebral space "i", attention is directed to drilling a bore in the first lateral side of the intervertebral space "i". The cutting depth of drill instrument 100 is adjusted as desired (i.e., to correspond to the length of the fusion implant) by adjusting collars 108, 110. With the T-handle 500 mounted to drill instrument 100, the instrument is introduced into the axial bore of retractor Sleeve 12 and advanced to contact the anterior surface of the vertebral bodies, "$V_1$, $V_2$". Drill 100 is advanced into the intervertebral space "i"adjacent the first lateral side by rotating T-handle 500 such that drill bit 106 shears the soft tissue and cuts the bone of the adjacent vertebrae "$V_1$, $V_2$" thereby forming a bore which extends into the adjacent vertebrae "$V_1$, $V_2$". Drill 100 is then removed from retractor sleeve 12.

Figure 11:
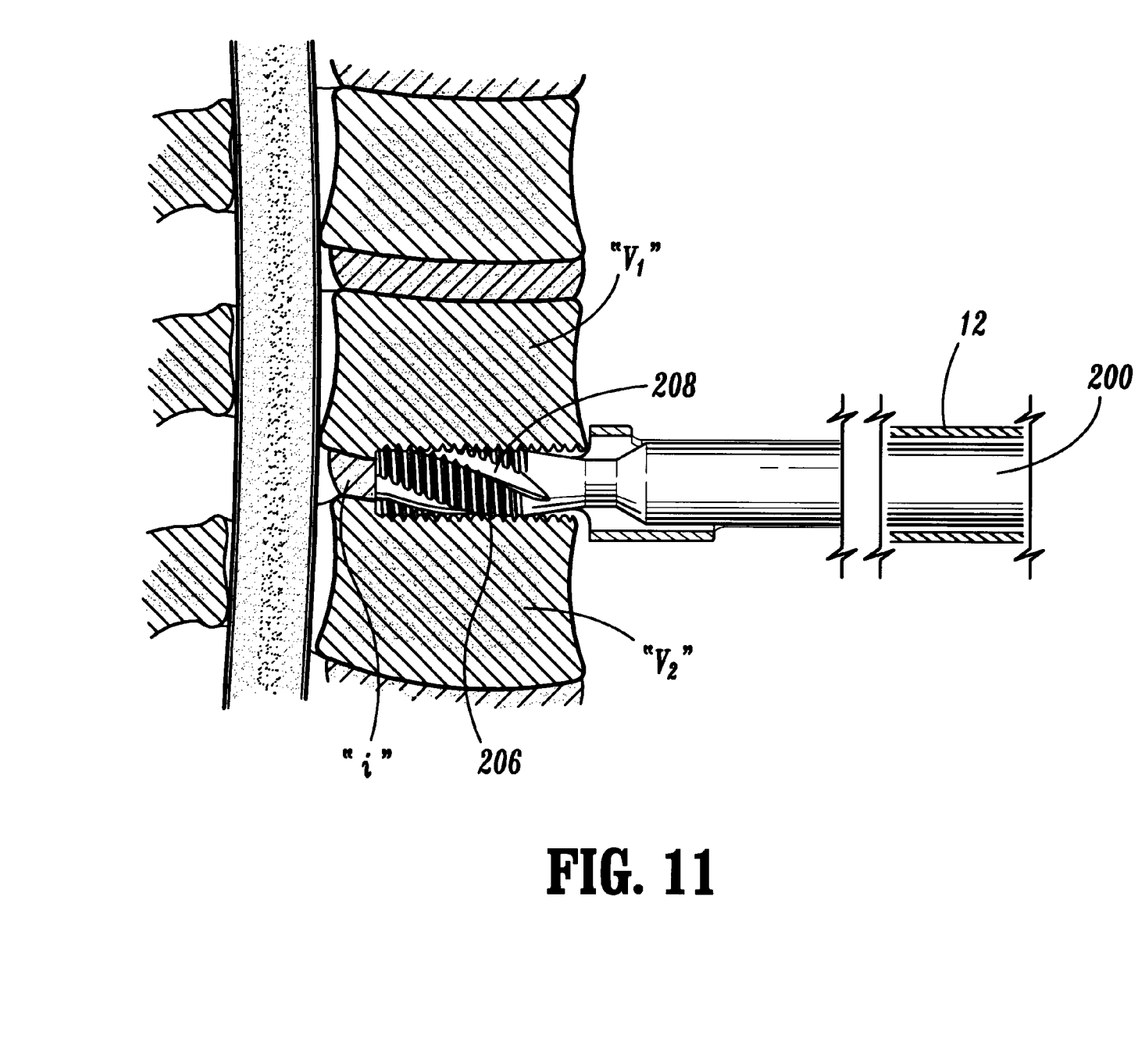
FIG. 11 is a view similar to the view of FIG. 10 illustrating insertion of the tap instrument within the retractor for tapping the bore formed in the first lateral side.

Referring now to FIG. 11, tap instrument 200 is selected and attached to the T-handle 500. Tap instrument 200 is inserted into retractor sleeve 12 and positioned adjacent the drilled bore formed in the adjacent vertebrae "$V_1, V_2$" by the surgical drill 100. With retractor sleeve 12 as a direct guide, T-handle 500 is rotated in while simultaneously applying sufficient downward pressure on the T-handle 500 to advance the tap instrument 200 and promote even purchase into the endplates. Upon advancement of the tap instrument 200, the deburred bone chips collect within conveyance channel 208 of tapping head 206, and are conveyed proximally during rotational movement of the tapping head 206 away from the tapping site. Tap instrument 200 is advanced into the bone until the desired depth has been achieved, which occurs when the distal end of tapping head 208 "bottoms out" on the bone. When tap instrument 200 reaches the appropriate depth, the tap instrument 200 is rotated via T-handle 500 in an opposite direction to back the instrument out of the bore. It is to be appreciated that in procedures where a self-tapping implant is utilized the tapping of the bore with tap instrument 200 is not necessary.

Figure 12:
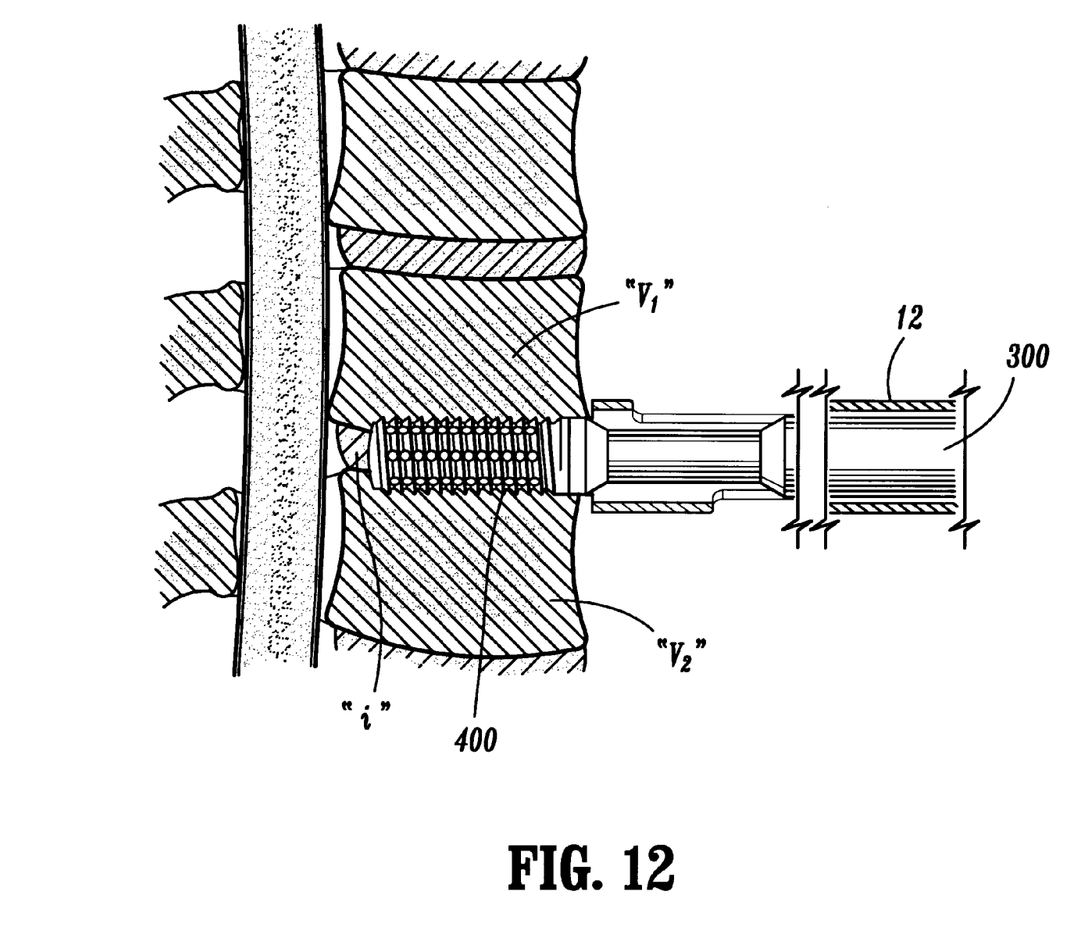
FIG. 12 is a view similar to the view of FIG. 11 illustrating insertion of the implant insertion instrument with mounted fusion implant within the retractor to mount the implant within the tapped bore.

With reference now to FIG. 12, attention is focused on the insertion of fusion implant 400. To insert the fusion implant, cage body 402 of the fusion implant 400 is mounted onto insertion instrument 300 by positioning the cage body 402 onto mounting collar 306 of the instrument to permit spring ball detent mechanism 308 to releasably engage corresponding structure of the implant body 402. This assembly is attached to T-handle 500. Insertion instrument 300 with mounted cage body 402 is inserted into retractor sleeve 12 of retractor 10 and the cage body 402 is positioned within the tapped bore by rotating insertion instrument 300 in the direction depicted in FIG. 12. Cage body 402 is advanced until it is completely seated with the bore as shown in FIG. 12. Insertion instrument 300 is then removed from retractor 10.

At this point in the procedure, bone growth inducing substances may be harvested from, e.g., the iliac crest, and packed into the cage body 402 of implant 400 until the cage body 402 is completely filled with bone growth inducing substances. An end cap may then be mounted to the cage body 202. Retractor 10 is then removed.

Figure 13:
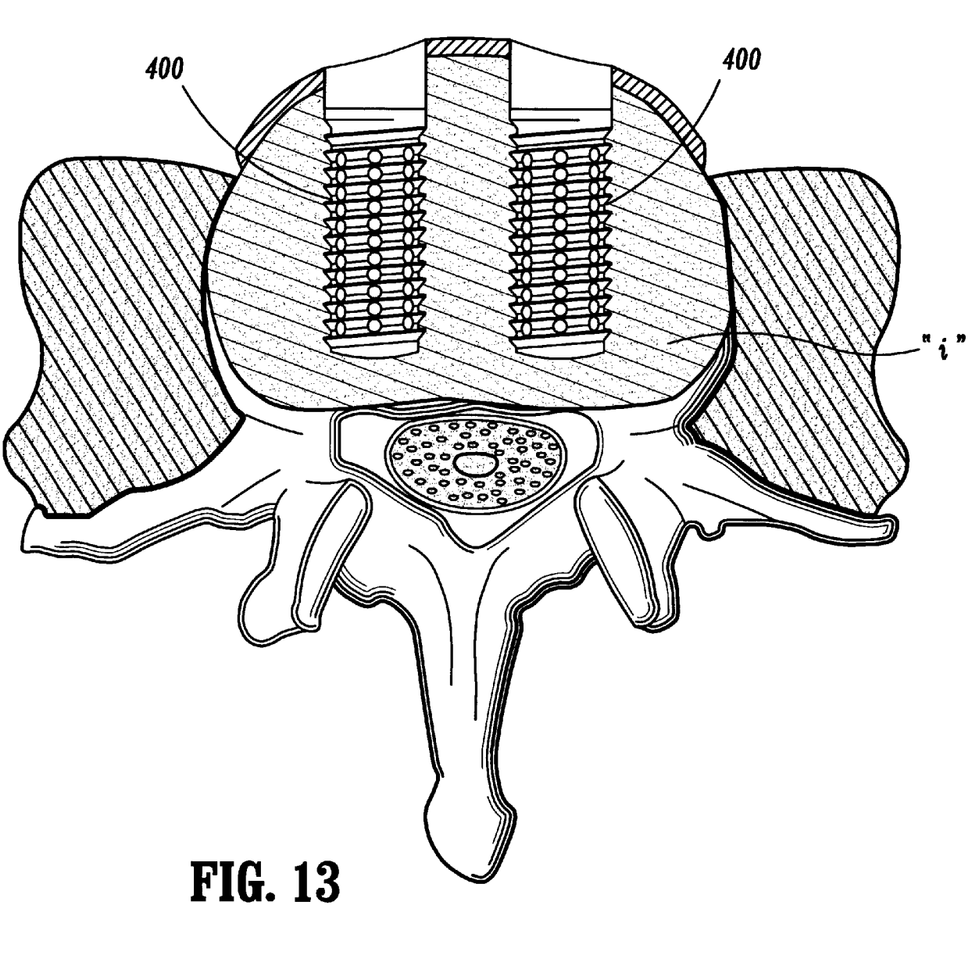
FIG. 13 is a cross-sectional view illustrating the insertion of two implants within the intervertebral space.

FIG. 13 illustrates the two lateral fusion implants 200 inserted within the intervertebral space in accordance with the afore-described procedure.

While the above description contains many specifics, these specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. An apparatus for facilitating fusion of adjacent vertebrae, which comprises:
   a retractor including a retractor sleeve having proximal and distal ends and defining a longitudinal axis, the retractor sleeve defining a longitudinal passageway for reception of surgical instrumentation, the retractor sleeve having first and second retractor arms extending distally therefrom in a general longitudinal direction, each retractor arm having first and second opposed supporting surfaces for engaging respective adjacent opposed vertebrae, each retractor arm defining a dimension between the first and second supporting surfaces sufficient to distract the opposed vertebrae upon insertion thereof; and
   a retractor introducer positionable within the longitudinal passageway, the retractor introducer including an elongated member defining proximal and distal ends and having a distal introducer head, the introducer head having a retractor arm insert, the retractor arm insert having a cross-sectional dimension to substantially occupy the inner area defined by the retractor arms of the retractor, the retractor arm insert having sufficient rigidity to advance within the tissue portions thereby facilitating placement of the first and second retractor arms of the retractor between the vertebral portions in distracting engagement therewith.

2. An apparatus according to claim 1 wherein the introducer head of the retractor introducer defines a proximal portion, the proximal portion having a cross-sectional dimension generally corresponding to the internal dimension of the retractor sleeve to substantially minimize entry of tissue within the retractor sleeve during placement between the opposed vertebrae.

3. An apparatus according to claim 2 wherein the cross-sectional dimension of the proximal portion of the introducer head is slightly less than the internal dimension of the retractor sleeve.

4. An apparatus according to claim 1 wherein the retractor introducer includes engaging structure to cooperate with corresponding engaging structure of the retractor sleeve to rotatably fix the retractor introducer and retractor sleeve.

5. An apparatus according to claim 4 wherein the engaging structure of the retractor introducer includes at least one pin, the one pin receivable within a corresponding groove of the retractor sleeve.

6. An apparatus according to claim 4 wherein the retractor introducer includes a first flange intermediate the proximal and distal end portions of the elongated member, the first flange in contacting engagement with the proximal end of the retractor sleeve wherein the retractor introducer and retractor sleeve move concurrently during placement within the opposed vertebrae.

7. An apparatus according to claim 6 wherein the retractor introducer includes a second flange adjacent the proximal end of the elongated member, the second flange dimensioned to receive impact of a hammer.

8. An apparatus according to claim 1 wherein the retractor sleeve includes at least one longitudinal opening in communication within the longitudinal passageway to receive surgical instrumentation.

9. An apparatus according to claim 1 wherein the retractor sleeve includes at least one longitudinal planar surface portion to minimize a cross-sectional dimension of the retractor sleeve.

10. An apparatus according to claim 9 wherein the retractor sleeve includes diametrically opposed longitudinal planar surface portions.

11. An apparatus according to claim 1, wherein the retractor introducer includes at least one spacer to create a gap between the retractor introducer and the retractor arms of the retractor sleeve.

12. A method for performing a surgical procedure, comprising the steps of:
   providing a surgical retractor including a sleeve member defining a longitudinal axis, the sleeve member including proximal and distal end portions and defining an axial opening therethrough to receive instrumentation, the distal end portion configured for insertion at least partially into an intervertebral space between adjacent opposed vertebrae and having two spaced apart retractor arms, each retractor arm including first and second supporting surfaces laterally displaced with respect to each other and to the longitudinal axis;
   positioning a retractor introducer within the axial opening of the retractor, the retractor introducer including an elongated member having a distal introducer head, the distal introducer head having a retractor arm insert arranged to be disposed between the retractor arms of the retractor sleeve in the mounted condition of the retractor introducer and having sufficient rigidity to facilitate advancement within tissue;

impacting the proximal end of the retractor introducer to drive the retractor arm insert of the retractor introducer and the retractor arms of the retractor within the intervertebral space whereby the first supporting surface of each retractor arm engages one vertebrae and the second supporting surface of each retractor arm engages the other vertebrae such that the adjacent opposed vertebrae are laterally displaced whereby the retractor arm insert facilitates entry of the retractor arms into the intervertebral space;

removing the retractor introducer; and performing the surgical spinal procedure.

13. The method according to claim 12 wherein the distal introducer head includes a proximal portion, the proximal portion having a cross-sectional dimension generally corresponding to the internal dimension of the retractor sleeve and wherein, during the step of impacting, the proximal portion of the distal introducer head substantially minimizes entry of tissue within the retractor sleeve.

14. The method according to claim 13 including the step of rotatably fixing the retractor introducer relative to the retractor sleeve by engaging cooperating structure of the retractor introducer and the retractor sleeve.

15. The method according to claim 13 wherein the step of performing includes introducing surgical instrumentation within the axial opening of the sleeve member, the surgical instrumentation being utilized to perform the surgical procedure.

16. The method according to claim 15 wherein the step of performing includes introducing a fusion implant through the axial opening of the sleeve member and between the distracted vertebrae to effect fusion thereof.

17. The method according to claim 12 wherein the sleeve member includes at least one slot defined in an outer wall surface portion thereof and wherein the step of performing includes introducing surgical instrumentation within the slot to perform the surgical procedure.

* * * * *